United States Patent
Ihara et al.

(10) Patent No.: US 7,511,002 B2
(45) Date of Patent: Mar. 31, 2009

(54) OIL-IN-WATER EMULSION AND PROCESS FOR PRODUCING THE SAME

(75) Inventors: Takeshi Ihara, Wakayama (JP); Ikuo Sugano, Wakayama (JP)

(73) Assignee: Kao Corporation, Tokyo (JP)

( * ) Notice: Subject to any disclaimer, the term of this patent is extended or adjusted under 35 U.S.C. 154(b) by 325 days.

(21) Appl. No.: 11/113,979

(22) Filed: Apr. 26, 2005

(65) Prior Publication Data
US 2005/0245423 A1 Nov. 3, 2005

(30) Foreign Application Priority Data
Apr. 27, 2004 (JP) ............... 2004-131472

(51) Int. Cl.
- *C11D 1/66* (2006.01)
- *C11D 3/20* (2006.01)
- *C11D 3/37* (2006.01)
- *C11D 3/43* (2006.01)
- *A61K 8/73* (2006.01)

(52) U.S. Cl. .............. 510/121; 510/122; 510/128; 510/151; 510/159; 510/417; 510/421; 510/432; 510/470; 510/475; 510/505; 424/401; 424/70.11; 424/70.12; 424/70.13; 424/70.31

(58) Field of Classification Search ............ 510/121, 510/122, 128, 151, 159, 417, 421, 432, 470, 510/475, 505; 424/401, 70.11, 70.12, 70.13, 424/70.31
See application file for complete search history.

(56) References Cited

U.S. PATENT DOCUMENTS

| 5,912,294 | A | 6/1999 | Schade |
| 6,541,614 | B1 * | 4/2003 | Nagasawa et al. .......... 536/18.3 |

FOREIGN PATENT DOCUMENTS

| EP | 1191039 A1 | 3/2002 |
| EP | 1369102 | * 12/2003 |
| EP | 1369102 A1 | 12/2003 |
| JP | 5-294989 A | 11/1993 |
| JP | 6-72851 A | 3/1994 |
| JP | 10-338714 A | 12/1998 |
| JP | 2003-226612 A | 8/2003 |
| WO | WO-97/31950 A1 | 9/1997 |
| WO | WO 00/73351 | * 12/2000 |

OTHER PUBLICATIONS

English language abstract of JP 2003-040765 (Feb. 13, 2003).
Kitahara Fumio et al. "Saishin koroido kagaku" (New Colloid Chemistry) pp. 44-45 published Oct. 20, 1990.
"Development of emulsion technology and emulsifier" (Nyu-ka gijutsu to nyu-ka zai no kaihatsu) pp. 78-81. Published on May 22, 1998 by CMC publisher.

* cited by examiner

*Primary Examiner*—Brian P Mruk
(74) *Attorney, Agent, or Firm*—Birch, Stewart, Kolasch & Birch, LLP

(57) ABSTRACT

The invention relates to an oil-in-water emulsion obtained by mixing (a) a polymer compound having, in a side chain, a group represented by formula (1):

$$-(OX)_n\text{-}E^2\text{-}R \qquad (1)$$

wherein X represents a C1 to C6 divalent saturated hydrocarbon group, n is a number of 5 to 300, $E^2$ is an ether linkage or an ester linkage, and R represents a C4 to C30 hydrocarbon group, (b) a water-soluble polyol, (c) a nonionic surfactant, (d) a hydrophobic compound, and water and diluting the resulting mixture with water and a process for producing the same.

10 Claims, No Drawings

OIL-IN-WATER EMULSION AND PROCESS FOR PRODUCING THE SAME

FIELD OF THE INVENTION

The present invention relates to an oil-in-water emulsion and a process for producing the same.

BACKGROUND OF THE INVENTION

To blend a hydrophobic compound such as oil stably as an emulsion is an important technique in products such as cosmetics and perfumes. Generally, emulsified particles in an emulsion using a low-molecular surfactant are small and relatively stable, but in a solution system in the presence of a large amount of a surfactant such as detergent, their stability is lost and emulsification is destroyed. Accordingly, even if a hydrophobic compound useful for the surface of skin and hair to be washed is blended as an emulsion, the hydrophobic compound is emulsified with a surfactant used as a detergent, thus deteriorating foaming of the detergent. In this case, the intentionally blended hydrophobic compound is also emulsified with a surfactant used as the detergent, and thus almost all of the blended hydrophobic compound is washed away, so there is a problem that after use, the hydrophobic compound rarely remains on the washed surface.

Accordingly, JP-A 2003-226612 discloses an oil-in-water emulsion which is stable in a system in the presence of a large amount of a surfactant such as a detergent, that is, excellent in resistance to a surfactant solution, can be compounded with a detergent without deteriorating fundamental performance such as foaming, and is excellent in feel upon application onto the skin, as well as a process for producing the same.

SUMMARY OF THE INVENTION

The present invention relates to an oil-in-water emulsion obtained by mixing (a) a polymer compound having, in a side chain, a group represented by formula (1) (referred to hereinafter as group (1)):

$$-(OX)_n-E^2-R \qquad (1)$$

wherein X represents a C1 to C6 linear or branched divalent saturated hydrocarbon group, n is a number of 5 to 300, Xs whose number is n may be the same or different, $E^2$ represents an ether linkage (—O—) or an ester linkage (—OCO— or —COO—), and R represents a C4 to C30 linear or branched hydrocarbon group which may be substituted with a hydroxy group, (b) a water-soluble polyol, (c) a nonionic surfactant, (d) a hydrophobic compound, and water and diluting the resulting mixture with water, and a process for producing the same.

DETAILED DESCRIPTION OF THE INVENTION

In JP-A 2003-226612 supra, the emulsified particles have a large diameter, thus causing the problem of creaming in low-density products.

The present invention relates to an oil-in-water emulsion having a small emulsified particle diameter, which is excellent in resistance to a surfactant solution, has oil droplets stably dispersed therein and is maintained in the form of a stable emulsion even in the presence of a surfactant at high concentration, as well as a process for producing the same.

The present inventors utilized a polymer compound having a specific group in a part of its side chain, to prepare a specific composition containing the same, a nonionic surfactant and a hydrophobic compound, and they found that an emulsion of the hydrophobic compound excellent in stability can be obtained by diluting the composition with water, and the present invention was thereby completed.

[Component (a)]

The polymer compound as component (a) in the present invention is preferably a polymer compound having a molecular weight of 10,000 to 10,000,000, more preferably 10,000 to 2,000,000, furthermore preferably 30,000 to 1,500,000. In the group (1), X is a C2 to C4 alkylene group, more preferably an ethylene group. n is preferably a number of 5 to 200, more preferably 8 to 120. R is preferably a C4 to C30 alkyl group, more preferably a C6 to C25 alkyl group.

The component (a) includes the following (i) and (ii). (i) A polysaccharide derivative having the group (1), and (ii) a water-soluble synthetic polymer compound having a molecular weight of 10,000 to 2,000,000, having the group (1) whose number is 0.0001 to 0.1 on the average per main-chain constituent monomer unit.

The polysaccharide derivative (i) is preferably a polysaccharide derivative obtained by replacing a part or the whole of hydrogen atoms of hydroxy groups in a polysaccharide or a polysaccharide derivative by the following group (A) (referred to hereinafter as polysaccharide derivative (i-1)) Group (A) represented by the formula (2):

$$-E^1-(OX)_{n1}-E^2-R \qquad (2)$$

wherein $E^1$ represents a C1 to C6 linear or branched divalent saturated hydrocarbon group which may be substituted with a hydroxy or oxo group, n1 is a number of 8 to 300, X, $E^2$ and R each have the same meaning as defined above, and Xs whose number is n1 may be the same or different.

The polysaccharide or its derivative used in the present invention includes polysaccharides such as cellulose, guar gum, starch, pullulan, dextran, fructane, mannan, agar, carrageenan, chitin, chitosan, pectin, alginic acid and hyaluronic acid, as well as derivatives thereof substituted with a methyl group, ethyl group, hydroxyethyl group, hydroxypropyl group etc. The constituent monosaccharide residue can be substituted with one or more of these substituent groups. Examples of the polysaccharide derivatives include hydroxyethyl cellulose, hydroxyethylethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum, hydroxypropylmethyl starch etc. Among these polysaccharides and derivatives thereof, cellulose, starch, hydroxyethyl cellulose, methyl cellulose, ethyl cellulose and hydroxypropyl cellulose are preferable, and particularly hydroxyethyl cellulose is preferable. The weight-average molecular weight of these polysaccharides or derivatives thereof is preferably in the range of 10,000 to 10,000,000, more preferably 100,000 to 5,000,000, still more preferably 200,000 to 2,000,000.

$E^1$ in the group (A) is preferably a C2 to C3 linear or branched divalent saturated hydrocarbon group which may be substituted with a hydroxy or oxo group, and preferable examples include ethylene, propylene, trimethylene, 2-hydroxytrimethylene, 1-hydroxymethylethylene, 1-oxoethylene, 1-oxotrimethylene, 1-methyl-2-oxoethylene etc. X is preferably a C2 or C3 linear or branched divalent saturated hydrocarbon group, and preferable examples include ethylene, propylene and trimethylene. The number of moles of (—OX—) added on the average, represented by n1, is preferably 8 to 120, more preferably 10 to 60, from the viewpoint of the thickening effect and emulsification stability. X whose number is n1 may be the same or different. $E^2$ is an ether linkage or an ester linkage, preferably an ether linkage. R is preferably a C5 to C25, particularly C6 to C20, linear or branched alkyl group which may be substituted with a hydroxy group, or is preferably an unsubstituted alkyl group, particularly an unsubstituted linear alkyl group, from the viewpoint of stability. Preferable examples include an octyl group, decyl group, dodecyl group, tetradecyl group, hexadecyl group, octadecyl group, isostearyl group etc.

The degree of substitution with the group (A) in the polysaccharide derivative (i-1) of the present invention is preferably in the range of 0.0001 to 1.0, more preferably 0.0005 to 0.5, still more preferably 0.001 to 0.1.

The polysaccharide derivative (i-1) of the present invention may be substituted not only with the group (A) but also with at least one group selected from the following groups (B), (C) and (D). Hydrogen atoms in hydroxy groups in the groups (A) to (D) may further be substituted with the groups (A) to (D).

(B) a C1 to C5 sulfoalkyl group which may be substituted with a hydroxy group, or a salt thereof, (C) a C2 to C6 carboxyalkyl group which may be substituted with a hydroxy group, or a salt thereof, or (D) a group represented by the formula (3):

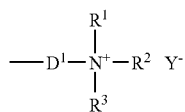

(3)

wherein $D^1$ represents a C1 to C6 linear or branched divalent saturated hydrocarbon group which may be substituted with a hydroxy group, $R^1$, $R^2$ and $R^3$ may be the same or different and each represent a C1 to C3 linear or branched alkyl group which may be substituted with a hydroxy group, and $Y^-$ represents a hydroxy ion, a halogen ion or an organic acid ion.

The group (B) includes a 2-sulfoethyl group, 3-sulfopropyl group, 3-sulfo-2-hydroxypropyl group, 2-sulfo-1-(hydroxymethyl) ethyl group etc., among which a 3-sulfo-2-hydroxypropyl group is preferable from the viewpoint of safety and production. A part or the whole of these groups (B) may be salts with alkali metals or alkaline earth metals such as Na, K, Ca, Mg etc. or with organic cations such as amines, ammonium etc. The degree of substitution with the groups (B) is preferably in the range of 0 to 1.0, more preferably 0 to 0.8, still more preferably 0 to 0.5, per constituent monosaccharide residue.

The group (C) includes a carboxymethyl group, carboxyethyl group, carboxypropyl group, carboxybutyl group, carboxypentyl group etc., among which a carboxymethyl group is preferable from the viewpoint of safety and production. A part or the whole of these groups (C) may be salts with alkali metals or alkaline earth metals such as Na, K, Ca, Mg etc. or with organic cations such as amines, ammonium etc. The degree of substitution with the groups (C) is preferably in the range of 0 to 1.0, more preferably 0 to 0.8, still more preferably 0 to 0.5, per constituent monosaccharide residue.

$D^1$ in the group (D) is preferably a C2 to C3 linear or branched divalent saturated hydrocarbon group which may be substituted with a hydroxy group, and preferable examples include ethylene, propylene, trimethylene, 2-hydroxytrimethylene, 1-hydroxymethylethylene etc. $R^1$, $R^2$ and $R^3$ include a methyl group, ethyl group, propyl group, 2-hydroxyethyl group etc., among which a methyl group and an ethyl group are preferable. In the groups represented by $Y^-$, the halogen ion includes a chlorine ion, bromine ion, iodine ion etc., and the organic acid ion includes $CH_3COO^-$, $CH_3CH_2COO^-$, $CH_3(CH_2)_2COO^-$ etc. $Y^-$ is preferably a hydroxy ion, a chlorine ion or a bromine ion. The degree of substitution with the groups (D) is preferably in the range of 0 to 0.5, more preferably 0 to 0.3, per constituent monosaccharide residue.

The substitution of the polysaccharide or its derivative with the groups (A) to (D), that is, the polyoxyalkylation, sulfoalkylation, carboxyalkylation or cationization thereof, can be carried out by methods described in WO 00/73351.

When cellulose or a derivative thereof is used as a starting polysaccharide (or its derivative) of the polysaccharide derivative (i-1) in the present invention, its repeating unit is represented by the following formula (6):

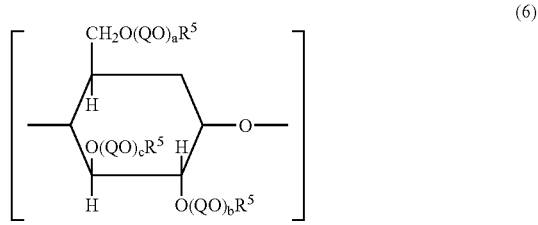

(6)

wherein $R^5$ represents a group selected from a hydrogen atom, methyl group, ethyl group, hydroxyethyl group, hydroxypropyl group, the group (A), the group (B), the group (C) and the group (D), Q represents a C2 to C4 alkylene group, a, b and c are the same or different and each represent a number of 0 to 10, the QO group, $R^5$ group, a, b and c may be the same or different in a repeating unit or among repeating units, and hydroxyl groups in the groups (A) to (D) may be further substituted with other groups (A) to (D), provided that at least one of $R^5$ in the molecule is the group (A).

The water-soluble synthetic polymer compound (ii) is a compound with a molecular weight of 10,000 to 2,000,000 having the group (1) whose number is 0.0001 to 0.1 on the average per main-chain constituent monomer unit, and the group (1) is preferably the group of formula (1) wherein X is an ethylene group, n is a number of 5 to 200, and R is a C4 to C30 linear or branched alkyl group. The average number of groups (1) per main-chain constituent monomer unit is more preferably 0.001 to 0.05, and the molecular weight is more preferably 30,000 to 1,500,000.

The water-soluble synthetic polymer compound (ii) can be obtained by reacting a compound represented by the formula (7):

$E^3$-(OX)$_n$-$E^2$-R  (7)

wherein $E^3$ is a C3 to C6 epoxylated alkyl group, a C1 to C6 linear or branched halogenated alkyl group whose hydroxyl group may be substituted, a carboxyl group, a C2 to C6 carboxyalkyl group or a derivative thereof, and X, n, R and $E^2$ each have the same meaning as defined above, with a hydroxy-containing water-soluble synthetic polymer compound such as polyvinyl alcohol and polyglycidol. Alternatively, the compound (ii) can be obtained by copolymerizing a water-soluble monomer with a monomer having a C4 to C30 hydrophobic group via a linking chain of 5 to 200 oxyethylene (EO) units.

The water-soluble monomer includes compounds represented by the formula (8):

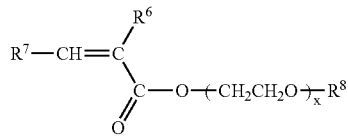

wherein $R^6$, $R^7$ and $R^8$ are the same or different and each represent a hydrogen atom or a methyl group, and x represents a number of 2 to 100, or compounds represented by the formula (9):

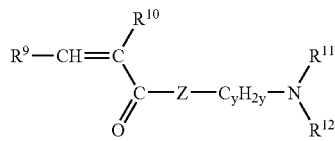

wherein $R^9$ and $R^{10}$ are the same or different and each represent a hydrogen atom or a methyl group, $R^{11}$ and $R^{12}$ each represent a methyl group or an ethyl group, y represents 0 or an integer of 2 to 5, Z represents a —N($R^{13}$)— group ($R^{13}$ is a hydrogen atom or a methyl group), an oxygen atom or a direct bond, and examples thereof include methoxypolyethylene glycol monomethacrylate, methoxypolyethylene glycol monoacrylate, polyethylene glycol monomethacrylate, polyethylene glycol monoacrylate, N,N-dimethylaminoethyl acrylate, N,N-dimethylaminopropyl acrylamide, N,N-dimethyl acrylamide etc., and these compounds can be synthesized by methods known in the art.

The monomer having a C4 to C30 hydrophobic group via a linking chain of 5 to 200 EO units includes compounds represented by the formula (10):

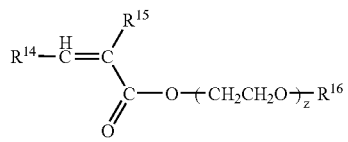

wherein $R^{14}$ and $R^{15}$ are the same or different and each represent a hydrogen atom or a methyl group, z represents a number of 5 to 200, and $R^{16}$ represents a C4 to C30, preferably C8 to C30, linear or branched alkyl group which may be substituted with a hydroxy group, and examples thereof include lauroxy polyethylene glycol monoacrylate, stearoxy polyethylene glycol monomethacrylate etc., and these compounds can be synthesized by methods known in the art.

[Component (b)]

The water-soluble polyol as the component (b) in the present invention is a polyhydric alcohol having at least 2 hydroxyl groups in its molecule, and specific examples include alkylene glycols such as ethylene glycol, propylene glycol, 1,3-butylene glycol, 1,4-butylene glycol etc., polyalkylene glycols such as dipropylene glycol etc., sugar alcohols such as glucose, maltose, maltitose, sucrose, fructose, xylitol, sorbitol, maltotriose, threitol etc., glycerin, polyglycerin, erythritol, and starch-decomposed reduced alcohol, and one or two or more thereof are used.

[Component (c)]

The nonionic surfactant as the component (c) in the present invention includes compounds represented by the formula (4) or (5):

$$R^4\text{-}E^2\text{-}(XO)_m\text{—}H \qquad (4)$$

wherein $E^2$ and X each have the same meaning as defined above, $R^4$ represents a C8 to C30 linear or branched, saturated or unsaturated hydrocarbon group or cholesteryl group, m represents a number of 5 to 20 on the average, and Xs whose number is m may be the same or different.

wherein $R^4$ has the same meaning as defined above.

In the nonionic surfactants represented by the formula (4) or (5), $R^4$ is a C8 to C30, preferably C8 to C20, linear or branched, saturated or unsaturated hydrocarbon group or cholesteryl group. Specific examples include an octyl group, decyl group, dodecyl group, tetradecyl group, hexadecyl group, octadecyl group, 2-ethylhexyl group, isodecyl group, isocetyl group, isostearyl group, hexadecyl group, heptylundecyl group, octyldodecyl group, oleyl group, cholesteryl group etc. The number of moles of added XO on the average in the formula (4) is 5 to 20, more preferably 5 to 15.

[Component (d)]

The hydrophobic compound as the component (d) in the present invention includes higher alcohols, sterols, silicones, fluorine-based oils, oily components etc. compounded to improve the functions and added value of toiletries.

The higher alcohols include, for example, benzyl alcohol, isocetyl alcohol, hexadecyl alcohol, phenylethyl alcohol, cetanol, stearyl alcohol, oleyl alcohol, 2-octyl dodecanol etc., among which cetanol and stearyl alcohol are particularly preferable.

The sterols include, for example, cholesterol, cholesteryl isostearate, provitamin $D_3$, campesterol, stigmastanol, cholesteryl alkenylsuccinate (JP-A 5-294989) etc. Among these, cholesterol, cholesteryl isostearate and cholesteryl alkenylsuccinate are particularly preferable.

The silicones include those incorporated usually into toiletries, including not only octamethyl polysiloxane, methyl polysiloxane, highly polymerized methyl polysiloxane and methylphenyl polysiloxane, but also methyl polycyclosiloxane (e.g. octamethyl cyclotetrasiloxane), trimethylsiloxy silicic acid, and modified silicones such as alkyl-modified silicone, polyether/alkyl-modified silicone, amino-modified silicone, fluorine-modified silicone, alkyl glyceryl ether-modified silicone, and the modified organopolysiloxane described in JP-A 6-72851.

The fluorine-based oils are preferably perfluoro organic compounds which are liquid at ordinary temperatures, such as perfluoropolyether, fluorine-modified silicone etc., and examples include perfluorodecalin, perfluorooctane, perfluorononane, perfluoropentane, perfluoropolyether etc.

The oily components may be volatile or non-volatile, and examples include hydrocarbons such as solid or liquid paraffin, Vaseline, crystal oil, squwalane etc.; ester oils such as eucalyptus oil, peppermint oil, sunflower oil, tallow, olive oil, carnauba wax, glycerin monostearate, glycerin distearate, isopropyl palmitinate, butyl stearate, neopentyl glycol dicaprylate, diethyl phthalate, myristyl lactate, diisopropyl adipate, cetyl myristate, 1-isostearoyl-3-myristoyl glycerol, 2-octyldodecyl myristate, neopentyl glycol di-2-ethylhexanoate, glycerol triisostearate, glyceryl di-paramethoxycinnamate-mono-2-ethylhexanoate etc.; higher aliphatic acids such as stearic acid, palmitic acid, oleic acid etc.; natural essential oils such as rosemary, rooibos, royal jelly, Winter bloom etc., and functional oily substances such as lignan, vitamin E, oil-soluble vitamin C, vitamin A derivatives, ceramides, ceramide analogs, oil-soluble UV absorber etc.

[Oil-In-Water Emulsion and Process for Producing the Same]

The oil-in-water emulsion of the present invention can be produced by mixing the components (a), (b), (c) and (d) and water, and diluting the resulting mixture with water, wherein 2 to 50 parts by weight of the component (b), 0.1 to 10 parts by weight of the component (c), 0.01 to 70 parts by weight of the component (d) and 5 to 30 parts by weight of water are preferably mixed to give composition (1) which is then diluted with water. The weight ratio of the component (b) to water in the composition (1), that is, the component (b)/water, is preferably 10/90 to 99/1, more preferably 10/90 to 90/10. To obtain the composition (1), the component (b) may be previously mixed with water to form an aqueous solution of water-soluble polyol and then mixed with other components.

In a more preferable embodiment of the present invention, the components (a), (b) and (c) and water are first mixed to give a composition (1a) which is then mixed with the component (d) to give the composition (1). In this case, it is preferable that in the composition (1a), the content of the component (a) is 1 to 10 wt %, the content of the component (b) is 10 to 90 wt %, the content of the component (c) is 0.1 to 20 wt %, and the content of water is 10 to 90 wt %. The component (b)/water ratio by weight is preferably 10/90 to 90/10. In this case, it is more preferable that the component (b) and water are first mixed to prepare an aqueous solution of water-soluble polyol, and then the aqueous solution is mixed with the component (a) preferably under stirring, followed by adding the component (c), to produce the composition (1a). By this production method, a stable oil-in-water emulsion having a small emulsion particle diameter can be prepared.

The amount of the component (d) mixed with the composition (1a) is preferably 0.01 to 70 parts by weight, more preferably 0.1 to 50 parts by weight, still more preferably 1.0 to 45 parts by weight, based on 1 part by weight of the component (a) contained in the composition (1a). Although the mixing method is not particularly limited, the component (d) may be added all at once, may be added continuously little by little or may be added several times in predetermined divided portions to the composition (1a) under suitable mechanical mixing force. The dropping speed or the frequency of addition in divided portions is not particularly limited, but is preferably regulated so as to attain an excellent mixed state. The whole of the predetermined amount of the component (d) is mixed with the composition (1a) to give the composition (1).

In another preferable embodiment of the present invention, the composition (1) can be prepared in the following manner. That is, the components (a) and (d) are mixed to prepare the composition (1b). The amount of the component (d) in the composition (1b) is preferably 0.01 to 70 parts by weight, more preferably 0.1 to 50 parts by weight, still more preferably 1.0 to 45 parts by weight, based on 1 part by weight of the component (a) contained in the composition (1b). Then, the composition (1b), the component (b) and water are mixed under stirring, followed by further adding the component (c), to produce the composition (1). In this case, the component (b) and water may first mixed to prepare an aqueous solution of water-soluble polyol, followed by mixing the aqueous solution with the composition (1b) under stirring. The content of the component (b) in the composition (1) is preferably 2 to 50 parts by weight, more preferably 2 to 40 parts by weight, still more preferably 4 to 35 parts by weight, based on 1 part by weight of the component (a). Although the mixing method is not particularly limited, the aqueous polyol solution may be added all at once, may be added continuously little by little or may be added several times in predetermined divided portions to the composition (1b) under suitable mechanical mixing force. The dropping speed or the frequency of addition in divided portions is not particularly limited, but is preferably regulated so as to attain an excellent mixed state. The whole of the predetermined amount of the aqueous polyol solution is mixed therewith, and then the component (c) is added thereto, to give the composition (1).

The composition (1) prepared in the manner described above is then diluted with water to give the oil-in-water emulsion of the present invention. The mixing method upon dilution with water is not particularly limited, and the composition (1) is mixed with water under suitable mechanical force depending on the viscosity of the composition (1) and the amount of water. With respect to the amount of water mixed, the composition (1)/water ratio by weight is preferably in the range of 1/99 to 99/1, more preferably 1/99 to 65/35, still more preferably 1/99 to 50/50.

The average particle diameter of emulsified particles containing the component (d), present in the oil-in-water emulsion of the present invention, is preferably 0.1 to 5.0 μm, more preferably 0.3 to 3 μm, still more preferably 0.5 to 2 μm. The average particle diameter of emulsified particles is a value determined by particle size distribution measurement with laser scattering, which is specifically a value determined by using LA-910 (manufactured by Horiba Ltd.). In this measurement, 0.5 g emulsion is diluted with 99.5 g physiological saline and then measured at room temperature.

The oil-in-water emulsion of the present invention can be used as such in cosmetics, massage cosmetics and skincare products, but may contain various additives usually used in these products, for example a surfactant, a dispersant, a solvent, a perfume, a dye, an inorganic salt, a preservative, an antioxidant and a pH regulator, in order to increase the added value of the products. Even if a surfactant is contained, the oil-in-water emulsion of the present invention exhibits excellent stability without particularly causing a change in viscosity with time and a change in outward appearance such as separation etc.

EXAMPLES

The present invention is described in more detail by reference to the Examples below. The Examples are set forth for illustrating the present invention and not intended to limit the present invention.

In the following examples, the degree of substitution with the group (A) in the polymer compound was determined by the Zeisel method [D. G. Anderson, Anal. Chem. 43, 894 (1971)], while the degrees of substitution with the groups (B), (C) and (D) were determined by a colloid titration method. In the following examples, the "degree of substitution" or "substitution degree" refers to the average number of substituent groups per constituent monosaccharide residue or per constituent monomer unit.

Preparation Example 1

Preparation of Polysaccharide Derivative 1

80 g of hydroxyethyl cellulose having a weight-average molecular weight of about 800,000 and a hydroxyethyl substitution degree of 1.8 (HEC-QP15000H manufactured by Union Carbide Corporation), 640 g isopropyl alcohol and 2.0 g p-toluenesulfonic acid were mixed to prepare slurry and stirred at room temperature for 30 minutes in a nitrogen atmosphere. 15 g of a compound represented by the following formula (11):

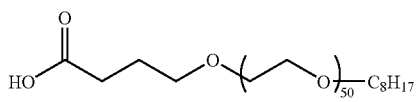

(11)

was added thereto, and the mixture was polyoxyalkylenated by reaction at 80° C. for 8 hours. After the reaction was finished, the reaction solution was neutralized with 48% aqueous sodium hydroxide, and the reaction product was separated by filtration. The reaction product was washed twice with 500 g of 80% isopropyl alcohol, then twice with 500 g isopropyl alcohol, and dried at 70° C. for one day under reduced pressure, to give 73.4 g polyoxyalkylenated hydroxyethyl cellulose (referred to as polysaccharide derivative 1). The degree of substitution with the group (A) in the polysaccharide derivative 1 was 0.010.

Preparation Example 2

Preparation of Polysaccharide Derivative 2

80 g potato starch (manufactured by Katayama Chemical, Inc.), 640 g of 50% isopropyl alcohol and 5.5 g of 48% aqueous sodium hydroxide were mixed to prepare slurry and stirred at room temperature for 30 minutes in a nitrogen atmosphere. 19.0 g of a compound represented by the following formula (12):

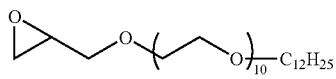

(12)

was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 500 g of 50% isopropyl alcohol, then twice with 500 g acetone, and dried at 70° C. for one day under reduced pressure, to give 69.4 g polyoxyalkylenated starch (referred to as polysaccharide derivative 2). The degree of substitution with the group (A) in the polysaccharide derivative 2 was 0.005.

Preparation Example 3

Preparation of Polysaccharide Derivative 3

20.0 g of the polysaccharide derivative 2 prepared in Preparation Example 2, 200 g of 70% isopropyl alcohol, 42.6 g of sodium 3-chloro-2-hydroxypropanesulfonate and 18.0 g of 48% aqueous sodium hydroxide were mixed and sulfonated at 50° C. for 5 hours. After the reaction was finished, the reaction solution was neutralized with acetic acid, and the reaction product was separated by filtration. The reaction product was washed 3 times with 400 g of 70% isopropyl alcohol and twice with 300 g isopropyl alcohol and then dried at 70° C. for one day under reduced pressure, to give 38.3 g polyoxyalkylenated and sulfonated starch (referred to as polysaccharide derivative 3). The degree of substitution with 3-sulfo-2-hydroxypropyl group (group (B)) in the polysaccharide derivative 3 was 0.301.

Preparation Example 4

Preparation of Polysaccharide Derivative 4

35.5 g of the polysaccharide derivative 2 prepared in Preparation Example 2, 350 g of 70% isopropyl alcohol and 2.4 g of 48% aqueous sodium hydroxide were mixed to prepare slurry and stirred at room temperature for 30 minutes in a nitrogen atmosphere. 25.1 g sodium monochloroacetate and 18.0 g of 48% aqueous sodium hydroxide were added thereto, and the mixture was carboxymethylated at 50° C. for 5 hours. After the reaction was finished, the reaction solution was neutralized with acetic acid, and the reaction product was separated by filtration. The reaction product was washed 3 times with 400 g of 70% isopropyl alcohol and twice with 300 g isopropyl alcohol and then dried at 70° C. for one day under reduced pressure, to give 33.8 g polyoxyalkylenated and carboxymethylated starch (referred to as polysaccharide derivative 4). The degree of carboxymethylation of the polysaccharide derivative 4 (the degree of substitution with the group (C)) was 0.48.

Preparation Example 5

Preparation of Polysaccharide Derivative 5

35.5 g of the polysaccharide derivative 2 prepared in Preparation Example 2, 350 g of 70% isopropyl alcohol and 2.4 g of 48% aqueous sodium hydroxide were mixed to prepare slurry and stirred at room temperature for 30 minutes in a nitrogen atmosphere. 7.0 g of 60% aqueous (3-chloro-2-hydroxypropyl) trimethyl ammonium chloride and 2.0 g of 48% aqueous sodium hydroxide were added thereto, and the mixture was cationized at 50° C. for 1 hour. After the reaction was finished, the reaction solution was neutralized with acetic acid, and the reaction product was separated by filtration. The reaction product was washed 3 times with 400 g of 70% isopropyl alcohol and twice with 300 g isopropyl alcohol and then dried at 70° C. for one day under reduced pressure, to give 34.2 g polyoxyalkylenated and cationized starch (referred to as polysaccharide derivative 5). The degree of cationization of the polysaccharide derivative 5 (the degree of substitution with the group (D)) was 0.10.

Preparation Example 6

Preparation of Polysaccharide Derivative 6

80 g of hydroxyethyl cellulose having a weight-average molecular weight of 1,500,000 and a hydroxyethyl substitution degree of 1.8 (HEC-QP100MH manufactured by Union Carbide Corporation), 640 g of 80% isopropyl alcohol and 5.34 g of 48% aqueous sodium hydroxide were mixed to prepare slurry and stirred at room temperature for 30 minutes in a nitrogen atmosphere. 12.78 g of a compound represented by the following formula (13):

(13)

was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 500 g isopropyl alcohol and then dried at 60° C. for one day under reduced pressure, to give 72.0 g polyoxyalkylenated hydroxyethyl cellulose (referred to as polysaccharide derivative 6). The degree of substitution with the group (A) in the polysaccharide derivative 6 was 0.004.

Preparation Example 7

Preparation of Polysaccharide Derivative 7

80 g of hydroxyethyl cellulose having a weight-average molecular weight of 1,500,000 and a hydroxyethyl substitution degree of 1.8 (HEC-QP100MH manufactured by Union Carbide Corporation), 640 g of 80% isopropyl alcohol and 5.34 g of 48% aqueous sodium hydroxide were mixed to prepare slurry and stirred at room temperature for 30 minutes in a nitrogen atmosphere. 21.7 g of a compound represented by the following formula (14):

(14)

was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 500 g isopropyl alcohol and then dried at 60° C. for one day under reduced pressure, to give 74.0 g polyoxyalkylenated hydroxyethyl cellulose (referred to as polysaccharide derivative 7). The degree of substitution with the group (A) in the polysaccharide derivative 7 was 0.004.

Preparation Example 8

Preparation of Polysaccharide Derivative 8

80 g of hydroxyethyl cellulose having a weight-average molecular weight of 800,000 and a hydroxyethyl substitution degree of 1.8 (HEC-QP15000H manufactured by Union Carbide Corporation), 640 g of 80% isopropyl alcohol and 5.34 g of 48% aqueous sodium hydroxide were mixed to prepare slurry and stirred at room temperature for 30 minutes in a nitrogen atmosphere. 13.7 g of a compound represented by the following formula (15):

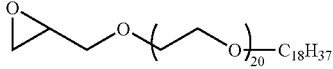

(15)

was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 500 g isopropyl alcohol and then dried at 60° C. for one day under reduced pressure, to give 69.0 g polyoxyalkylenated hydroxyethyl cellulose (referred to as polysaccharide derivative 8). The degree of substitution with the group (A) in the polysaccharide derivative 8 was 0.003.

Preparation Example 9

Preparation of Polysaccharide Derivative 9

80 g of hydroxyethyl cellulose having a weight-average molecular weight of 500,000 and a hydroxyethyl substitution degree of 1.8 (HEC-QP4400H manufactured by Union Carbide Corporation), 640 g of 80% hydrous isopropyl alcohol and 5.34 g of 48% aqueous sodium hydroxide were mixed to prepare slurry and stirred at room temperature for 30 minutes in a nitrogen atmosphere. 12.78 g of a compound represented by the formula (13) above was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 500 g isopropyl alcohol and then dried at 60° C. for one day under reduced pressure, to give 73 g polyoxyalkylenated hydroxyethyl cellulose (referred to as polysaccharide derivative 9). The degree of substitution with the group (A) in the polysaccharide derivative 9 was 0.004.

Preparation Example 10

Preparation of Polysaccharide Derivative 10

160 g hydroxyethyl cellulose having a weight-average molecular weight of 200,000 and a hydroxyethyl substitution degree of 2.5 (NATROZOL 250G manufactured by Hercules Incorporated), 1280 g of hydrous 80% isopropyl alcohol and 9.8 g of 48% aqueous sodium hydroxide were mixed to prepare slurry, which was then stirred at room temperature for 30 minutes in a nitrogen atmosphere. 21.2 g of a compound represented by the formula (13) above was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 700 g isopropyl alcohol and then dried at 60° C. for one day under reduced pressure, to give 151 g polyoxyalkylenated hydroxyethyl cellulose (referred to as polysaccharide derivative 10). The degree of substitution with the group (A) in the polysaccharide derivative 10 was 0.009.

Preparation Example 11

Preparation of Polysaccharide Derivative 11

160 g hydroxyethyl cellulose having a weight-average molecular weight of 200,000 and a hydroxyethyl substitution degree of 2.5 (NATROZOL 250G manufactured by Hercules Incorporated), 1280 g of hydrous 80% isopropyl alcohol and 9.8 g of 48% aqueous sodium hydroxide were mixed to prepare slurry, which was then stirred at room temperature for 30 minutes in a nitrogen atmosphere. 31.8 g of a compound represented by the formula (13) above was added thereto and the mixture was polyoxyalkylenated by reaction at 80° C. for 8 hours. After the reaction was finished, the reaction solution was neutralized with acetic acid, and the reaction product was separated by filtration. The reaction product was washed twice with 700 g isopropyl alcohol and then dried at 60° C. for one day under reduced pressure, to give 152 g polyoxyalkylenated hydroxyethyl cellulose (referred to as polysaccharide derivative 11). The degree of substitution with the group (A) in the polysaccharide derivative 11 was 0.014.

Preparation Example 12

Preparation of Polysaccharide Derivative 12

160 g hydroxyethyl cellulose having a weight-average molecular weight of 200,000 and a hydroxyethyl substitution degree of 2.5 (NATROZOL 250M manufactured by Hercules Incorporated), 1280 g of hydrous 80% isopropyl alcohol and 9.8 g of 48% aqueous sodium hydroxide were mixed to prepare slurry, which was then stirred at room temperature for 30 minutes in a nitrogen atmosphere. 47.7 g of a compound represented by the formula (13) above was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 700 g isopropyl alcohol and then dried at 60° C. for one day under reduced pressure, to give 153 g polyoxyalkylenated hydroxyethyl cellulose (referred to as polysaccharide derivative 12). The degree of substitution with the group (A) in the polysaccharide derivative 12 was 0.021.

Preparation Example 13

Preparation of Polysaccharide Derivative 13

160 g hydroxyethyl cellulose having a weight-average molecular weight of 200,000 and a hydroxyethyl substitution degree of 2.5 (NATROZOL 250M, manufactured by Hercules Incorporated), 1280 g of hydrous 80% isopropyl alcohol and 9.8 g of 48% aqueous sodium hydroxide were mixed to prepare slurry, which was then stirred at room temperature for 30 minutes in a nitrogen atmosphere. 56.8 g of a compound represented by the formula (13) above was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 700 g isopropyl alcohol and then dried at 60° C. for one day under reduced pressure, to give 155 g polyoxyalkylenated hydroxyethyl cellulose (referred to as polysaccharide derivative 13). The degree of substitution with the group (A) in the polysaccharide derivative 13 was 0.025.

Preparation Example 14

Preparation of Polysaccharide Derivative 14

80 g hydroxyethyl cellulose having a weight-average molecular weight of 200,000 and a hydroxyethyl substitution degree of 2.5 (NATROZOL 250G, manufactured by Hercules Incorporated), 640 g of hydrous 80% isopropyl alcohol and 4.9 g of 48% aqueous sodium hydroxide were mixed to prepare slurry, which was then stirred at room temperature for 30 minutes in a nitrogen atmosphere. 19.02 g of a compound represented by the formula (15) above was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 500 g isopropyl alcohol and then dried at 60° C. for one day under reduced pressure, to give 74 g polyoxyalkylenated hydroxyethyl cellulose (referred to as polysaccharide derivative 14). The degree of substitution with the group (A) in the polysaccharide derivative 14 was 0.0037.

Preparation Example 15

Preparation of Polysaccharide Derivative 15

60 g hydroxyethyl cellulose having a weight-average molecular weight of 200,000 and a hydroxyethyl substitution degree of 2.5 (NATROZOL 250G, manufactured by Hercules Incorporated), 480 g of hydrous 80% isopropyl alcohol and 3.67 g of 48% aqueous sodium hydroxide were mixed to prepare slurry, which was then stirred at room temperature for 30 minutes in a nitrogen atmosphere. 39.45 g of a compound represented by the formula (14) above was added thereto, and the mixture was polyoxyalkylenated by reaction at 80° C. for 8 hours. After the reaction was finished, the reaction solution was neutralized with acetic acid, and the reaction product was separated by filtration. The reaction product was washed twice with 400 g isopropyl alcohol and then dried at 60° C. for one day under reduced pressure, to give 52 g polyoxyalkylenated hydroxyethyl cellulose (referred to as polysaccharide derivative 15). The degree of substitution with the group (A) in the polysaccharide derivative 15 was 0.0135.

Preparation Example 16

Preparation of Synthetic Polymer Compound 1

3 g polyglycidol having a weight-average molecular weight of 5400, 100 g dimethyl sulfoxide (DMSO) and 0.16 g granular NaOH were mixed and stirred at 70° C. After the solution became uniform, the solution was cooled. 0.765 g of a compound represented by the formula (13) above was added thereto at room temperature and aged at 80° C. for 8 hours. After cooling, the reaction solution was neutralized by adding 0.23 mL acetic acid. The DMSO was distilled away, and the resulting pale yellow viscous solid was washed with isopropyl alcohol (IPA) (30 mL×3). After drying under reduced pressure, 2.9 g of a polymer compound represented by formula (16) below (referred to as synthetic polymer compound 1) was obtained. The degree of substitution with the group (A) in the synthetic polymer compound 1 was 0.0053.

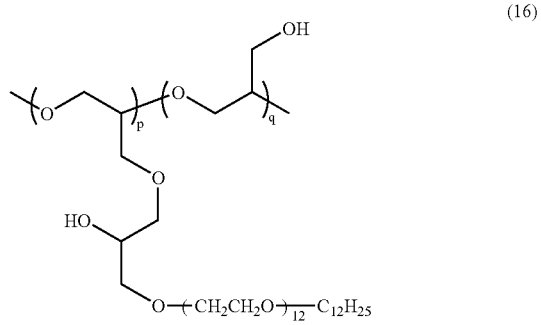

(16)

Preparation Example 17

Preparation of Synthetic Polymer Compound 2

20 g polyvinyl alcohol having an average polymerization degree of 2000, 200 g DMSO and 1.81 g granular NaOH were mixed and stirred at 70° C. After the solution became uniform, the solution was cooled. 1.87 g of a compound represented by the formula (13) above was added thereto at room temperature and aged at 80° C. for 8 hours. After cooling, the reaction solution was neutralized by adding 2.59 mL acetic acid. The reaction mixture was added to IPA. Precipitated white solids were filtered, and the resulting solids were washed with IPA (300 mL×3). After drying under reduced pressure, 19.0 g of a polymer compound represented by formula (17) below (referred to as synthetic polymer compound 2) was obtained. The degree of substitution with the group (A) in the synthetic polymer compound 2 was 0.0033.

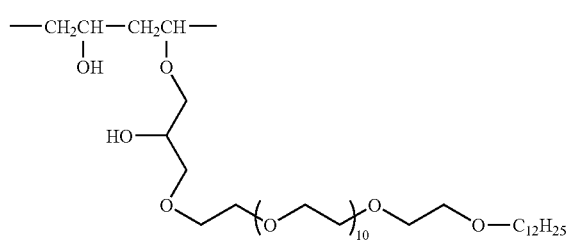

(17)

Preparation Example 18

Preparation of Synthetic Polymer Compound 3

97.1 g monomer A represented by the formula below, 20.7 g monomer B represented by the formula below, and 180 g ethanol were mixed. A nitrogen gas (20 mL/min., 1 hour) was blown into the resulting solution to degas the system which was then heated to 60° C. Thereafter, 82.8 g of (3%) solution of V-65 (polymerization initiator) in ethanol was added dropwise thereto while the temperature was kept at 60° C. Thereafter, the mixture was aged at 60° C. for 12 hours. After the reaction was finished, the resulting reaction mixture was dropped into 2 kg diisopropyl ether. The resulting white solids were separated by filtration and then washed with diiso- propyl ether (500 g×twice). After drying under reduced pressure, 105 g of a polymer compound represented by formula (18) (referred to as synthetic polymer compound 3) was obtained. The degree of introduction of the monomer B into the synthetic polymer compound 3, as determined by $^1$H-NMR, was 0.025. The weight-average molecular weight was 51000.

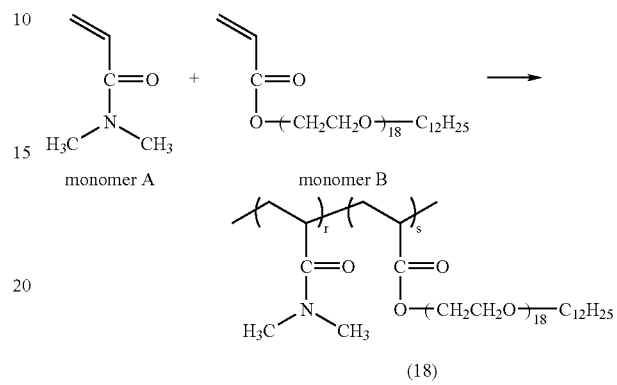

(18)

Preparation Example 19

Preparation of Synthetic Polymer Compound 4

501.8 g monomer C represented by the formula below, 20.7 g monomer B represented by the formula below, and 780 g ethanol were mixed. A nitrogen gas (40 mL/min., 1 hour) was blown into the resulting solution to degas the system which was then heated to 60 C. Thereafter, 82.8 g of (3%) solution of V-65 in ethanol was added dropwise thereto while the temperature was kept at 60° C. Thereafter, the mixture was aged at 60° C. for 12 hours. After the reaction was finished, the resulting reaction mixture was dropped into 5 kg diisopropyl ether. The resulting white solids were separated by filtration and then washed with diisopropyl ether (500 g×twice). After drying under reduced pressure, 490 g of a polymer compound represented by formula (19) (referred to as synthetic polymer compound 4) was obtained. The degree of introduction of the monomer B into the synthetic polymer compound 4, as determined by $^1$H-NMR, was 0.022. The weight-average molecular weight was 110000.

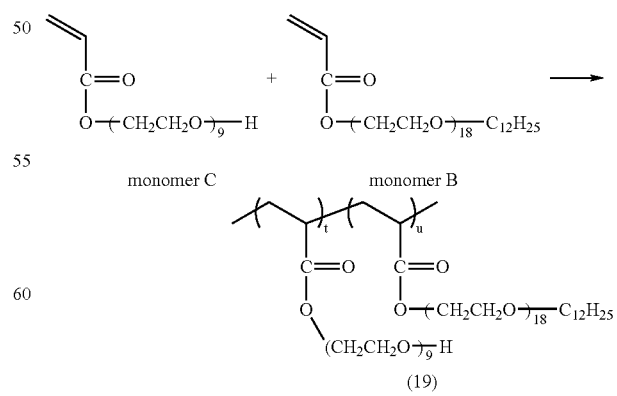

(19)

The following compounds were used as the nonionic surfactants in the Examples and Comparative Examples below.

• Nonionic surfactants (1), (2)

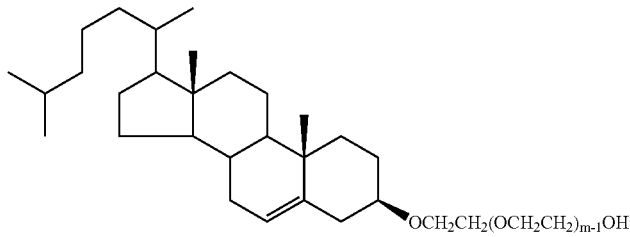

(1); m = 5
(2); m = 10

• Nonionic surfactants (3), (4)

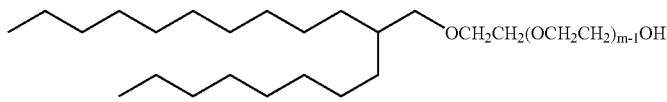

(3); m = 10
(4); m = 20

• Nonionic surfactant (5)

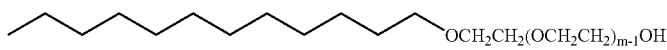

(5); m = 6

• Nonionic surfactant (6)

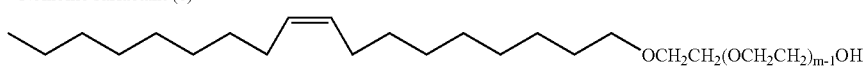

(6); m = 9

• Nonionic surfactant (7)

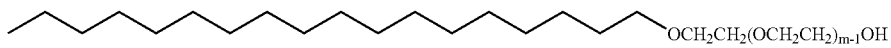

(7); m = 11

• Nonionic surfactant (8)

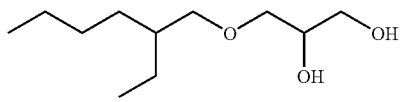

• Nonionic surfactant (9)

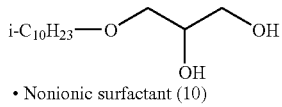

• Nonionic surfactant (10)

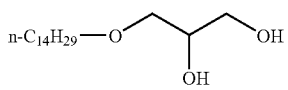

Examples 1 to 25

The component (a) and the aqueous polyol solution were mixed at 60° C. in a ratio shown in Tables 1 and 2, then dissolved uniformly under stirring at a rate of 300 rpm, and cooled to 30° C. Then, the component (c) was added dropwise thereto at the same stirring rate to give the composition (1a). Then, the component (d) was added dropwise thereto at 30° C. under stirring at 300 rpm (rounds per minute). After this addition was finished, the mixture was kept at the same stirring rate and temperature for 30 minutes or more. After ion exchange water was added thereto, the mixture was stirred for 30 minutes or more to give an oil-in-water emulsion. The resulting oil-in-water emulsion was evaluated for its emulsified state immediately after preparation, average emulsion particle diameter, and stability. The results are shown in Tables 1 and 2.

<Emulsified State Immediately after Preparation>

1 g of the resulting emulsion was diluted with 9 g of ion exchange water and then placed in a suitable amount on a slide glass, and the emulsified state of the composition was observed under a digital microscope (KEYENCE VH-8500).

<Average Emulsion Particle Diameter>

The average particle diameter of emulsified particles in the emulsion was determined by measuring a dilution of 0.5 g emulsion in 99.5 g physiological saline at room temperature with a laser scattering particle size distribution measuring instrument LA-910 manufactured by Horiba Ltd.

<Stability>

The emulsion was stored for 1 month at room temperature and at 40° C. respectively and then evaluated under the following criteria by observing the presence or absence of separation with naked eyes.
O : No separation was observed.
x : Separated.

TABLE 1

| | | | Example | | | | | | | | | | | | |
|---|---|---|---|---|---|---|---|---|---|---|---|---|---|---|---|
| | | | 1 | 2 | 3 | 4 | 5 | 6 | 7 | 8 | 9 | 10 | 11 | 12 | 13 |
| Oil-in-water type emulsion (part) | Component (a) | Polysaccharide derivative 3 | 0.5 | | | | | | | | | | | | |
| | | Polysaccharide derivative 6 | | 0.2 | | | | | | | | | | | |
| | | Polysaccharide derivative 8 | | | 0.2 | | | | | | | | | | |
| | | Polysaccharide derivative 9 | | | | 0.25 | 0.25 | 0.25 | | | | | | | |
| | | Polysaccharide derivative 10 | | | | | | | | 0.2 | | | | | |
| | | Polysaccharide derivative 11 | | | | | | | | | 0.2 | 0.2 | 0.2 | 0.2 | |
| | | Polysaccharide derivative 12 | | | | | | | | | | | | 0.3 | |
| | | Polysaccharide derivative 13 | | | | | | | | | | | | | 0.2 |
| | | Polysaccharide derivative 14 | | | | | | | | | | | | | |
| | | Synthetic polymer compound 1 | | | | | | | | | | | | | |
| | | Synthetic polymer compound 2 | | | | | | | | | | | | | |
| | | Synthetic polymer compound 3 | | | | | | | | | | | | | |
| | | Synthetic polymer compound 4 | | | | | | | | | | | | | |
| | Aqueous polyol solution | 86% glycerine | | 9 | 9 | 8 | | 8 | 9 | | | | | | |
| | | 70% glycerine | | | | | 8 | | | | 9 | 9 | 9 | | 9 |
| | | 70% 1,3-butylene glycol | | | | | | | | | | | | 5 | |
| | | 30% dipropyrene glycol | | | | | | | | | | | | 5 | |
| | | 50% propylene glycol | 10 | | | | | | | | | | | | |
| | Component (c) | (1) | | | | 0.2 | | | | | | | 0.1 | | |
| | | (2) | | | | | | | | 0.3 | | | | | |
| | | (3) | | | | | 0.2 | | | | | | | | |
| | | (4) | | | | | | | | | | | | 0.2 | |
| | | (5) | | | | | | | | | | | | | 0.5 |
| | | (6) | | | | | | 0.25 | | | | | | | |
| | | (7) | | | | | | | | | | | | | |
| | | (8) | 0.5 | 0.1 | | | | | | | | 0.5 | 0.4 | | |
| | | (9) | | | | | | | | | 0.1 | | | | |
| | | (10) | | | 0.2 | | | | | | | | | | |
| | Component (d) | Stearyl alcohol | | | | 7.5 | | | | | | | | | |
| | | Silicone oil*1 (KF96A 6cs) | | | | | 5 | | | 12 | | | | | |
| | | Perfluoropoly ether*2 (FOMBLINHCO4) | | | | | | | | | | 1 | | | |
| | | Sunflower oil | | 6 | 6 | | | | | | | 12 | | | |
| | | Oleic acid | | | | | | 7.5 | | | | | 2 | | |
| | | Squwalane | 3 | | | | | | | | | | | 3 | 4 |
| | | Olive oil | | | | | | | | | | | | | |
| | | 2-Ethylhexyl p-methoxycinnamate | | | | | | | 6 | | | | | | |
| | | Ion exchange water | 36 | 34.7 | 34.6 | 36.6 | 34.1 | 34 | 34.5 | 28.7 | 39.3 | 38.4 | 42.7 | 41.5 | 36.3 |
| Result of evaluation | | Emulsified state immediately after preparation | O/W | O/W | O/W | O/W | O/W | O/W | O/W | O/W | O/W | O/W | O/W | O/W | O/W |
| | | Average emulsion particle diameter (μm) | 1.5 | 2.0 | 1.5 | 1.1 | 1.2 | 1.0 | 1.1 | 0.9 | 1.1 | 1.0 | 1.0 | 1.1 | 1.2 |
| | | Stability (room temperature, for 1 month) | O | O | O | O | O | O | O | O | O | O | O | O | O |
| | | Stability (40° C., for 1 month) | O | O | O | O | O | O | O | O | O | O | O | O | O |

TABLE 2

| | | | Example | | | | | | | | | | | |
|---|---|---|---|---|---|---|---|---|---|---|---|---|---|---|
| | | | 14 | 15 | 16 | 17 | 18 | 19 | 20 | 21 | 22 | 23 | 24 | 25 |
| Oil-in-water type emulsion (part) | Component (a) | Polysaccharide derivative 3 | | | | | | | | | | | | |
| | | Polysaccharide derivative 6 | | | | | | 0.2 | | | | | | |
| | | Polysaccharide derivative 8 | | | | | | | | | | | | |
| | | Polysaccharide derivative 9 | | | | | | | 0.2 | | | | | |
| | | Polysaccharide derivative 10 | | | | | | | | | | | | |
| | | Polysaccharide derivative 11 | | | | | | | | 0.2 | 0.2 | 0.2 | 0.2 | 0.2 |
| | | Polysaccharide derivative 12 | | | | | | | | | | | | |
| | | Polysaccharide derivative 13 | | | | | | | | | | | | |
| | | Polysaccharide derivative 14 | 0.2 | | | | | | | | | | | |
| | | Synthetic polymer compound 1 | | 0.3 | | | | | | | | | | |
| | | Synthetic polymer compound 2 | | | 0.3 | | | | | | | | | |
| | | Synthetic polymer compound 3 | | | | 0.3 | | | | | | | | |
| | | Synthetic polymer compound 4 | | | | | 0.3 | | | | | | | |
| | Aqueous polyol solution | 86% glycerine | | | | | 3 | 9 | 9 | | | | | |
| | | 70% glycerine | 9 | | 3 | 3 | | | | 9 | 9 | 9 | 9 | |
| | | 70% 1,3-butylene glycol | | | | | | | | | | | | 9 |
| | | 30% dipropylene glycol | | | | | | | | | | | | |
| | | 50% propylene glycol | | 3 | | | | | | | | | | |
| | Component (c) | (1) | | | | | | | 0.5 | | 0.5 | | | |
| | | (2) | | | | | | 0.5 | | | 0.6 | | | |
| | | (3) | | | | | | | | | | 0.5 | | |
| | | (4) | | | | | | | | | | | | |
| | | (5) | | | | | | | | | | | | |
| | | (6) | | | 0.3 | 0.5 | | | 0.5 | | | | 0.5 | 1 |
| | | (7) | 0.5 | | | | | | | | | | | |
| | | (8) | | | | | | | | | | | | |
| | | (9) | | | | | | | | | | | | |
| | | (10) | | 0.2 | | | | | | | | | | |
| | Component (d) | Stearyl alcohol | | | | | | | | | | 8 | | |
| | | Silicone oil*¹ (KF96A 6cs) | | | | | | 4 | | | 6 | | | |
| | | Perfluoropoly ether*² (FOMBLINHCO4) | | | | | | | | | | | | |
| | | Sunflower oil | | 4 | 3 | | | | | | | | 12 | |
| | | Oleic acid | | | | | | | | | | | | |
| | | Squwalane | 4 | | | 3 | 5 | | | | 12 | | | 5 |
| | | Olive oil | | | | | | | 4 | | | | | |
| | | 2-Ethylhexyl p-methoxycinnamate | | | | | | | | | | | | |
| | | Ion exchange water | 36.3 | 42.5 | 43.4 | 43.2 | 41.2 | 36.3 | 36.3 | 28.3 | 34.2 | 32.3 | 28.3 | 34.8 |
| Result of evaluation | | Emulsified state immediately after preparation | O/W | O/W | O/W | O/W | O/W | O/W | O/W | O/W | O/W | O/W | O/W | O/W |
| | | Average emulsion particle diameter (μm) | 1.1 | 1.1 | 1.1 | 0.9 | 1.0 | 1.2 | 1.0 | 1.2 | 0.9 | 0.9 | 1.1 | 0.5 |
| | | Stability (room temperature, for 1 month) | ○ | ○ | ○ | ○ | ○ | ○ | ○ | ○ | ○ | ○ | ○ | ○ |
| | | Stability (40° C., for 1 month) | ○ | ○ | ○ | ○ | ○ | ○ | ○ | ○ | ○ | ○ | ○ | ○ |

*¹manufactured by Shin-Etsu Chemical Co., Ltd.
*²manufactured by Nikko Chemicals Examples 26 to 34

The components (a) and (d) were mixed in a ratio shown in Table 3 and then stirred at 30° C. under stirring at a rate of 300 rpm to prepare a dispersion of the components (a) and (d). Then, the aqueous polyol solution was added dropwise thereto at the same stirring rate at the same temperature. After this addition was finished, the mixture was kept for 1 hour or more under the same conditions as above. Thereafter, the reaction mixture was heated to 60° C. and stirred for 30 minutes at 300 rpm. After the mixture was cooled to 30° C., the component (c) was added dropwise thereto under stirring at the same rate. After this addition was finished, the reaction mixture was kept at the same stirring rate and temperature as above for 30 minutes or more. After ion exchange water was added thereto, the mixture was stirred for 30 minutes or more to give an oil-in-water emulsion. The resulting oil-in-water emulsion was evaluated for its emulsified state immediately after preparation, average emulsion particle diameter and stability in the same manner as in Example 1. The results are shown in Table 3.

TABLE 3

| | | | Example | | | | | | | | | |
|---|---|---|---|---|---|---|---|---|---|---|---|---|
| | | | 26 | 27 | 28 | 29 | 30 | 31 | 32 | 33 | 34 |
| Oil-in-water type emulsion (part) | Component (a) | Polysaccharide derivative 6 | 0.2 | | | | | | 0.25 | | |
| | | Polysaccharide derivative 9 | | 0.2 | 0.2 | | | | | 0.25 | |
| | | Polysaccharide derivative 11 | | | | 0.2 | 0.2 | 0.2 | | | 0.25 |
| | Aqueous polyol solution | 86% glycerine | 9 | 9 | 9 | | | | 9 | 9 | |
| | | 70% glycerine | | | | | | | | | 9 |
| | | 70% 1,3-butylene glycol | | | | 5 | | | | | |
| | | 30% dipropyrene glycol | | | | | 5 | | | | |
| | | 50% propylene glycol | | | | | | 5 | | | |
| | Component (c) | (1) | 0.5 | | | | | | | | |
| | | (3) | | | | | | | 0.5 | | |
| | | (6) | | | | 0.4 | | | | | |
| | | (8) | | 0.5 | | | 0.5 | | | | 0.5 |
| | | (9) | | | 0.2 | | | | | 0.3 | |
| | | (10) | | | | | | | 0.5 | | |
| | component (d) | Silicone oil*1 (KF96A 6cs) | | | | 8 | | | | | |
| | | Sunflower oil | | 4 | | | | | | | |
| | | Squalane | 4 | | | 8 | 8 | 6 | | | |
| | | Silicone oil*2 (KHS-7) | | | | | | | 8 | 10 | 12 |
| | | Ion exchange water | 36.3 | 36.3 | 32.6 | 36.4 | 36.3 | 38.3 | 32.25 | 30.45 | 28.25 |
| Result of evaluation | | Emulsified state immediately after preparation | O/W | O/W | O/W | O/W | O/W | O/W | O/W | O/W | O/W |
| | | Average emulsion particle diameter | 1.2 | 1.1 | 1.2 | 1.1 | 0.9 | 1.0 | 1.3 | 1.0 | 0.9 |
| | | Stability (room temperature, for 1 month) | ○ | ○ | ○ | ○ | ○ | ○ | ○ | ○ | ○ |
| | | Stability (40° C. for 1 month) | ○ | ○ | ○ | ○ | ○ | ○ | ○ | ○ | ○ |

*1 manufactured by Shin-Etsu Chemical Co., Ltd.
*2 manufactured by Shin-Etsu Chemical Co., Ltd.

Comparative Examples 1 to 7

Oil-in-water emulsions were obtained in the same manner as in Examples 1 to 25 except that the component (c) was not added. The oil-in-water emulsions were evaluated for their emulsified state immediately after preparation, average emulsion particle diameter and stability in the same manner as in Example 1. The results are shown in Table 4.

TABLE 4

| | | | Comparative example | | | | | | |
|---|---|---|---|---|---|---|---|---|---|
| | | | 1 | 2 | 3 | 4 | 5 | 6 | 7 |
| Oil-in-water type emulsion (part) | component (a) | Polysaccharide derivative 6 | | | | | 0.2 | | |
| | | Polysaccharide derivative 9 | 0.25 | 0.25 | | | | 0.2 | |
| | | Polysaccharide derivative 11 | | | 0.2 | 0.2 | | | 0.2 |
| | Aqueous polyol solution | 86% glycerine | 8 | 8 | | | 9 | 9 | |
| | | 70% glycerine | | | 9 | 9 | | | 9 |
| | Component (d) | Silicone oil*1 (KF96A 6cs) | 5 | | 12 | | 4 | | |
| | | Sunflower oil | | | | 12 | | | |
| | | Oleic acid | | 7.5 | | | | | |
| | | Squalane | | | | | | | 12 |
| | | Olive oil | | | | | | 4 | |
| | | Ion exchange water | 36.75 | 34.25 | 28.8 | 28.8 | 36.8 | 36.8 | 28.8 |
| Result of evaluation | | Emulsified state immediately after preparation | O/W | O/W | O/W | O/W | O/W | O/W | O/W |
| | | Average emulsion particle diameter (μm) | 13.0 | 14.0 | 13.0 | 12.0 | 16.0 | 13.0 | 14.0 |
| | | Stability (at room temperature for 1 month) | X | X | X | X | X | X | X |
| | | Stability (40° C. for 1 month) | X | X | X | X | X | X | X |

*1 manufactured by Shin-Etsu Chemical Co., Ltd.

Comparative Example 8

A composition having the same formulation as in Example 2 in Table 1 was prepared in the following manner.

The polysaccharide derivative 6 as the component (a) and 86% aqueous glycerin were mixed at 60° C., dissolved uniformly under stirring at a rate of 300 rpm and cooled to 30° C. to give composition (8a). Then, sunflower oil as the component (d) was added to the composition (8a) at 30° C. under stirring at 300 rpm. After sunflower oil was added, the mixture was kept at the same stirring rate and at the same temperature for 30 minutes or more, and then a necessary amount of ion exchange water containing the whole of the nonionic surfactant (8) as the component (c) was added thereto, and the mixture was stirred for 30 minutes or more to give an oil-in-water emulsion. The resulting oil-in-water emulsion was evaluated for its emulsified state immediately after preparation, average emulsion particle diameter and stability in the same manner as in Example 1, and as a result, an O/W emulsion was obtained, but its particle diameter was 13.0 μm, and thus particles in this emulsion could not be made small unlike the Examples in the present invention. With respect to stability, separation was observed during storage at room temperature and 40° C. for 1 month.

Comparative Example 9

A composition having the same formulation as in Example 1 in Table 1 was prepared in the following manner.

The polysaccharide derivative 3 as the component (a) and 50% aqueous propylene glycol were added to a necessary amount of ion exchange water (60° C.) under stirring at 300 rpm, to give composition (9a). The resulting composition (9a) was cooled to 30° C. under stirring at 300 rpm, and then the nonionic surfactant (8) as the component (c) was added thereto. Further, squwalane as the component (d) was added dropwise to the mixture at 30° C. under stirring at 300 rpm, and the mixture was kept at the same temperature and at the same stirring rate for 30 minutes or more, to give composition (9b). The resulting composition (9b) was not an oil-in-water emulsion and was separated into 2 phases, that is, squwalane and an aqueous phase.

The invention claimed is:

1. A process for producing an oil-in-water emulsion, said process comprising the steps of:
    mixing:
    (a) a polymer compound having, in a side chain, a group represented by formula (1)

wherein X represents a C1 to C6 linear or branched divalent saturated hydrocarbon group, n is a number of 5 to 300, Xs whose number is n may be the same as or different from one another, $E^2$ represents an ether linkage (—O—) or an ester linkage (—OCO— or —COO—), and R represents a C4 to C30 linear or branched hydrocarbon group which may be substituted with a hydroxy group,
    (b) a water-soluble polyol,
    (c) a nonionic surfactant,
    (d) a hydrophobic compound, and water; and then diluting the resulting mixture with water,
    so that the average emulsion particle diameter of the emulsion in the oil-in-water emulsion is 0.1 to 2 μm.

2. The process for producing an oil-in-water emulsion according to claim 1, wherein 2 to 50 parts by weight of the component (b), 0.1 to 10 parts by weight of the component (c), 0.01 to 70 parts by weight of the component (d) and 5 to 30 parts by weight of water are mixed with 1 part by weight of the component (a) to prepare composition (1) and composition (1) is then diluted with water.

3. The process for producing an oil-in-water emulsion according to claim 2, wherein the weight ratio of the component (b)/water in the composition (1) is 10/90 to 99/1.

4. The process for producing an oil-in-water emulsion according to claim 2 or 3, wherein the components (a), (b) and (c) and water are mixed with one another and then the component (d) is added to, and mixed with, the resulting mixture to produce composition (1) and composition (1) is then diluted with water.

5. The process for producing an oil-in-water emulsion according to claim 2 or 3, wherein the component (b) and water, and further the component (c), are added to, and mixed with, a mixture of the components (a) and (d) to produce composition (1) and composition (1) is then diluted with water.

6. The process for producing an oil-in-water emulsion according to claim 1, wherein the component (a) is a polysaccharide derivative having a group represented by the formula (1).

7. The process for producing an oil-in-water emulsion according to claim 6, wherein the polysaccharide derivative having a group represented by the formula (1) is a polysaccharide derivative obtained by replacing a part or the whole of hydrogen atoms of hydroxy groups in a polysaccharide or its derivative by the following group (A):

Group (A) represented by the formula (2):

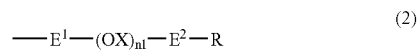

wherein $E^1$ represents a C1 to C6 linear or branched divalent saturated hydrocarbon group which may be substituted with a hydroxy or oxo group, n1 is a number of 8 to 300, X, $E^2$ and R each have the same meaning as defined in claim 1, and Xs whose number is n1 may be the same as or different from one another.

8. The process for producing an oil-in-water emulsion according to claim 1, wherein the component (a) is a water-soluble synthetic polymer compound having a molecular weight of 10,000 to 2,000,000, having a group whose number is 0.0001 to 0.1 on the average per main-chain constituent monomer unit, said group being represented by the formula (1) wherein X is an ethylene group, n is a number of 5 to 200, and R represents a C4 to C30 linear or branched alkyl group.

9. The process for producing an oil-in-water emulsion according to claim 1 or 6, wherein the component (c) is a compound represented by the formula (4):

wherein $E^2$ and X each have the same meaning as defined in claim 8, $R^4$ represents a C8 to C30 liner or branched, saturated or unsaturated hydrocarbon group or cholesteryl group, m represents a number of 5 to 20 on the average, and Xs whose number is m may be the same as or different from one another.

10. The process for producing an oil-in-water emulsion according to claim 1 or 6, wherein the component (c) is a compound represented by the formula (5):

wherein $R^4$ represents a C8 to C30 liner or branched, saturated or unsaturated hydrocarbon group or cholesteryl group.

* * * * *